US006342394B1

(12) United States Patent
Smith et al.

(10) Patent No.: US 6,342,394 B1
(45) Date of Patent: Jan. 29, 2002

(54) DIAGNOSIS OF AUTOIMMUNE ADRENAL DISEASE

(75) Inventors: Bernard Rees Smith; Jadwiga Furmaniak, both of Cardiff (GB)

(73) Assignee: RSR Limited, Cardiff (GB)

( * ) Notice: Subject to any disclaimer, the term of this patent is extended or adjusted under 35 U.S.C. 154(b) by 0 days.

(21) Appl. No.: 09/341,391

(22) PCT Filed: Nov. 27, 1998

(86) PCT No.: PCT/GB98/03566

§ 371 Date: Nov. 8, 1999

§ 102(e) Date: Nov. 8, 1999

(87) PCT Pub. No.: WO99/28752

PCT Pub. Date: Oct. 6, 1999

(30) Foreign Application Priority Data

Nov. 28, 1997 (GB) ............................................... 9725105

(51) Int. Cl.⁷ ............................................ G01N 33/564
(52) U.S. Cl. ..................... 436/506; 436/507; 436/536; 436/542
(58) Field of Search ................................ 436/507, 506, 436/537–542; 435/810

(56) References Cited

U.S. PATENT DOCUMENTS 4,198,389 A * 4/1980 Wadsworth
5,376,533 A    12/1994 Maclaren et al.

FOREIGN PATENT DOCUMENTS

GB    2256046 A  * 11/1992
WO    WO9425604    11/1994

* cited by examiner

*Primary Examiner*—Patrick J. Nolan
(74) *Attorney, Agent, or Firm*—Kohn & Associates (57) ABSTRACT

Diagnosis of overt, subclinical or potential autoimmune adrenal disease, by contacting a sample of body fluid with: (i) at least one epitope region of 21-hydroxylase which epitope region is essential for binding monoclonal or polyclonal antibodies to 21-hydroxylase and/or autoantibodies to 21-hydroxylase; and (ii) monoclonal or polycolonal antibodies to 21-hydroxylase. The degree of binding of the autoantibodies present in the sample to the relevant epitope region is monitored.

35 Claims, 2 Drawing Sheets

SEQUENCE LISTING

```
<160> NUMBER OF SEQ ID NOS: 6

<210> SEQ ID NO 1
<211> LENGTH: 15
<212> TYPE: PRT
<213> ORGANISM: Homo sapiens

<400> SEQUENCE: 1

Ala His Leu Asp Glu Thr Val Trp Glu Arg Pro His Glu Phe Trp
 1               5                  10                  15

<210> SEQ ID NO 2
<211> LENGTH: 15
<212> TYPE: PRT
<213> ORGANISM: Bovine

<400> SEQUENCE: 2

Ala His Leu Asp Glu Thr Val Trp Glu Gln Pro His Glu Phe Arg
 1               5                  10                  15

<210> SEQ ID NO 3
<211> LENGTH: 6
<212> TYPE: PRT
<213> ORGANISM: Homo sapiens

<400> SEQUENCE: 3

Pro Asp Arg Phe Leu Glu
 1               5

<210> SEQ ID NO 4
<211> LENGTH: 6
<212> TYPE: PRT
<213> ORGANISM: Bovine
```

-continued

```
<400> SEQUENCE: 4

Pro Asp Arg Phe Leu Glu
  1               5

<210> SEQ ID NO 5
<211> LENGTH: 5
<212> TYPE: PRT
<213> ORGANISM: Homo sapiens

<400> SEQUENCE: 5

Pro Tyr Lys Asp Arg
  1               5

<210> SEQ ID NO 6
<211> LENGTH: 5
<212> TYPE: PRT
<213> ORGANISM: Bovine

<400> SEQUENCE: 6

Thr Tyr Lys Asp Arg
  1               5
```

DIAGNOSIS OF AUTOIMMUNE ADRENAL DISEASE

CROSS REFERENCE TO RELATED APPLICATIONS

This application is a National Phase filing, which claims the benefit of priority under 35 U.S.C. Section 120 of PCT Patent Application Serial No. PCT/GB98/03566, filed Nov. 27, 1998, which is based upon British Serial No. 9725105.2, filed Nov. 28, 1997 both of which are incorporated herein by reference.

The present invention relates to diagnosis of overt, subclinical or potential autoimmune adrenal disease. Examples of autoimmune adrenal diseases include Addison's disease (AD) and autoimmune polyglandular syndrome (APS) type I and type II.

More especially, the present invention relates to use of the major autoantigen in autoimmune adrenal disease, human steroid 21-hydroxylase (21-OH) and to the epitopes on the 21-OH molecule reactive with 21-OH autoantibodies (Ab) in a patient's serum. The present invention concerns particular amino acid sequences of the 21-OH peptide, important for 21-OH Ab binding, and methods for using such sequences for diagnosis and prediction of the development of autoimmune adrenal disease.

The adrenal cortex of supra renal glands produce steroid hormones, such as cortisol and aldosterone. In addition, androgens (such as testosterone) are also secreted by the adrenal cortex.

Signs and symptoms of Addison's disease are related to the insufficiency of the adrenal cortex and include low blood pressure, muscle weakness, increased skin pigmentation and electrolyte imbalance. The severity of the symptoms depend on the extent of adrenal failure and if not treated, this disorder will inevitably lead to adrenocortical crisis and subsequent death.

Among the various causes of Addison's disease, the autoimmune origin is currently the most common. Autoantibodies to the adrenal cortex were first described in 1957 using the complement fixation technique. In 1988, an adrenal specific 55 kDa protein was immunoprecipitated from adrenal microsomes using Addison sera. This protein was subsequently shown to be human steroid 21-hydroxylase and identified to be the major adrenal autoantigen in different forms of autoimmune adrenal disease. Measurement of 21-OH Ab is a useful diagnostic tool in cases of suspected or overt adrenal failure and 21-OH Abs can be helpful markers of progression towards autoinmmune Addison's disease in patients with other organ-specific autoimmune diseases, such as type I diabetes, especially in children.

Previous studies have shown that autoantibody binding sites on 21-hydroxylase are in the main part conformational and are formed by the central and the C-terminal parts of the protein. Three fragments of 21-OH amino acid (AA) sequence (AA 164–356; 272–356 and 338–360) have been reported in U.S. Pat. No. 5,376,533 to be reactive with 21-OH Abs and potentially useful in specific diagnostic assays to identify the autoantibody associated with Addison's disease.

According to the present invention, we have determined that other parts of the 21-hydroxylase sequence are important for autoantibody binding in patients with different forms of autoimmune adrenal disease.

According to the present invention there is provided a method to aid in the diagnosis of overt, subclinical or potential autoimmune adrenal disease, said method comprising:

(a) providing a sample of body fluid from a subject;
(b) contacting the sample with
   (i) at least one epitope region of 21-hydroxylase, which epitope region is either present in said 21-hydroxylase or in a fragment thereof and which epitope region is essential for binding monoclonal or polyclonal antibodies to 21-hydroxylase and/or autoantibodies to 21-hydroxylase; and
   (ii) monoclonal or polyclonal antibodies to 21-hydroxylase; and
(c) monitoring the degree of binding of said autoantibodies present in said sample to said epitope region.

Depending on the assay system used, a substantial change in the amount of binding (a substantial increase or substantial decrease) of the autoantibodies to the relevant epitope region indicates that the subject may have autoimmune adrenal disease or be at risk of developing said disease.

In one embodiment of the present invention, the monoclonal or polyclonal antibodies may be immobilised to a solid phase; alternatively, at least one epitope region of 21-hydroxylase may be immobilised to a solid phase. The solid phase may be a magnetic or a non-magnetic material.

The monoclonal or polyclonal antibodies typically comprise any of human antibodies, rodent antibodies, rabbit antibodies or recombinant antibodies or parts or fragments thereof.

The relevant epitope region(s) may be directly labelled; alternatively, in some embodiments, the epitope region(s) may be indirectly labelled (for example, by binding the epitope region(s) to labelled monoclonal antibodies).

According to the present invention, 21-hydroxylase labeled with, for example, $^{125}$I is incubated with none, one, or more monoclonal or polyclonal antibodies to 21-hydroxylase. The antibodies are directed to epitope regions on 21-hydroxylase which preferably include amino acids 391 to 405 (SEQ ID No: 1 & 2), 406 to 411 (SEQ ID No: 3 & 4) and/or amino acids 335 to 339 (SEQ ID No: 5 & 6). These monoclonal or polyclonal antibodies bind to the epitope regions on the labeled 21-hydroxylase, thus preventing the subsequent binding of patient serum autoantibodies to the epitope regions. According to the invention, a mixture of labeled 21-hydroxylase (which therefore comprises labeled epitope regions of 21-hydroxylase) and monoclonal or polyclonal antibodies is contacted with the sample of body fluid from a patient (typically with autoantibodies to 21-hydroxylase). The ability of a particular monoclonal or polyclonal antibody to 21-hydroxylase to lower the binding of 21-hydroxylase autoantibodies to 21-hydroxylase indicates the presence of autoantibodies to the same epitope region as the particular monoclonal or polyclonal antibody.

The monoclonal or polyclonal antibody, which itself may be labeled, is selected for reactivity with epitope regions along the amino acid sequence of 21-hydroxylase, the relevant epitope regions preferably comprising amino acid sequence (AA) 391 to 405 (SEQ ID Nos: 1 & 2), (AA) 406 to 411 (SEQ ID No: 3 & 4) and/or (AA) 335 to 339 (SEQ ID No: 5 & 6).

The method according to the present invention preferably comprises monitoring the reactivity of autoantibodies to 21-hydroxylase in a subject's body fluid (such as serum, whole blood or amniotic fluid) with one or more of the three different epitope regions mentioned above. The reactivity with the three different epitope regions may be monitored individually or in combination.

According to the present invention, the components of the reaction, namely 21-hydroxylase or its relevant epitope region(s), and monoclonal or polyclonal antibodies to 21-hydroxylase, may be labelled with suitable radioisotopic or non-isotopic labels. Suitable isotopic labels include $^{125}I$, $^{35}S$, $^{14}C$ and $^{3}H$; suitable non-isotopic labels include enzymes, dyes, gold, chemiluminescent substances and fluorescent substances.

The reactivity between the various components may be monitored using a variety of methods, such as an enzyme linked immunosorbent assay (ELISA), solid or liquid phase radio-immunoassays (RIA), immunochromatographic assays, immunoprecipitation assays, or the like.

The following examples are used to further illustrate the present invention and are given by way of example only:

Plasmid Constructions

The full length 21-hydroxylase gene was cloned into pYES2.0 (Invitrogen) (pYES2/21-OH1) downstream of the T7 promoter. Various in frame deletions and truncations of the 21-hydroxylase gene were carried out using different restriction enzyme sites and the modified genes were cloned into pYES3, a derivation of pYES2.0. In addition, construct P21-OH14 was produced using PpumI restriction enzyme.

Table 1 shows the reactivity of full length and modified human steroid 21-hydroxylase with monoclonal antibodies.

TABLE 1

| | Modified 21-OH | | | Reaction with Monoclonal Antibodies | | | | |
|---|---|---|---|---|---|---|---|---|
| Construct | Enzyme Sites Used | Amino acids deleted | Region of deletion | M21-OH1 | M21-OH2 | M21-OH3 | M21-OH4 | M21-OH5 |
| P21-OH1 | None | None | C-terminal | + | + | + | + | + |
| P21-OH2 | StuI | 448–494 | C-terminal | + | + | + | + | + |
| P21-OH3 | BstXI | 418–494 | C-terminal | + | + | + | + | + |
| P21-OH4 | SauI | 381–494 | C-terminal | – | – | – | – | + |
| P21-OH12 | SauI/BstXI | 382–414 | Internal | – | – | – | – | + |
| P21-OH14 | PpumI | 335–494 | C-terminal | – | – | – | – | – |
| P21-OH5 | BprpI | 282–494 | C-terminal | – | – | – | – | – |

Figure 1:
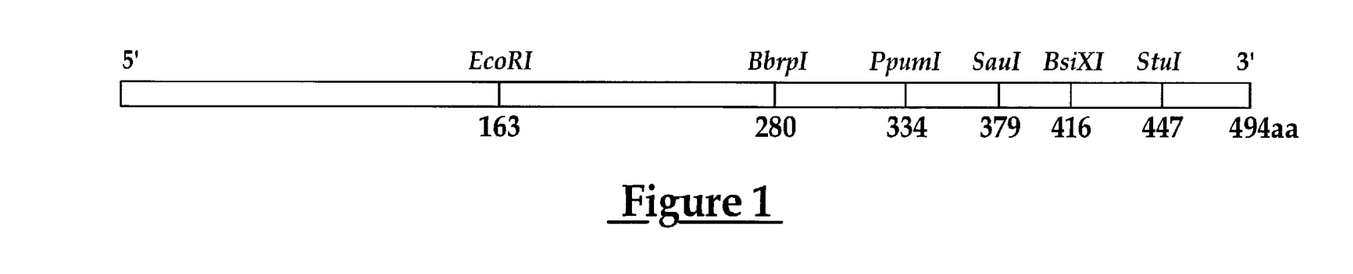
FIG. 1 is a schematic representation of the restriction enzyme sites on 21-hydroxylase.

Full length 21-hydroxylase cDNA was subcloned into the KpnI site of pTZ18F (pND21-OH1), a derivation of the vector pTZ18R (Pharmacia Biotech). The vector pTZ18F contained a specially designed, unique linker into AccI and HindIII sites which had stop codons in all three frames to ensure translation termination of all inserted genes. A series of 21-hydroxylase gene constructs with small stretches of gene sequence deleted (pND21-OH2-7) were generated from this construct using a Nested Deletion Kit (Pharmacia Biotech) (see FIG. 1). These constructs were sequenced by the dideoxy termination method using Sequenese Version 2.0 kit (United States Biochemical) and the M13 (–40) sequencing primer.

Table 2 outlines the various constructs and the reactivity of full length and modified human steroid 21-hydroxylase with monoclonal antibodies.

TABLE 2

| | | Reaction with Monoclonal Antibodies | | | | |
|---|---|---|---|---|---|---|
| Construct | Amino Acids Deleted | M21-OH1 | M21-OH2 | M21-OH3 | M21-OH4 | M21-OH5 |
| pND21-OH1 | None | + | + | + | + | + |
| pND21-OH2 | 448–494 | + | + | + | + | + |
| pND21-OH3 | 412–494 | + | + | + | + | + |
| pND21-OH4 | 406–494 | + | + | – | – | + |
| pND21-OH5 | 391–494 | – | – | – | – | + |

TABLE 2-continued

| Construct | Amino Acids Deleted | Reaction with Monoclonal Antibodies | | | | |
|---|---|---|---|---|---|---|
| | | M21-OH1 | M21-OH2 | M21-OH3 | M21-OH4 | M21-OH5 |
| pND21-OH6 | 360–494 | − | − | − | − | + |
| pND21-OH7 | 340–494 | − | − | − | − | + |
| pND21-OH8 | 335–494 | − | − | − | − | − |

Antibodies to 21-hydroxylase

A panel of 5 mouse monoclonal antibodies (MAbs) raised to human recombinant 21-hydroxylase expressed in *Escherichia coli* was produced at RSR Limited and used in the study. 21-hydroxylase MAb IgG was purified by affinity chromatography on Prosep-A (Bioprocessing Limited) and the purified IgG preparations were treated with either pepsin (Sigma) at an enzyme/protein ratio of 1/10 or mercuripapain (Sigma) at an enzyme/protein ratio of 1/10 and passed through a Prosep-A column to remove any intact IgG or Fc fragment from the Fab or F(ab')$_2$, respectively. Control IgG and Fab preparations were obtained from a TSH receptor (TSHR) mouse monoclonal antibody (RSR Limited). Rabbit antibody to 21-hydroxylase from RSR Limited was also used as a control in some experiments. Serum was obtained from 21-hydroxylase Ab positive patients (n=25) with:- APS type I (n=5), APS type II (n=5), isolated Addison's disease (n=5), 21-hydroxylase Ab positive patients with normal adrenal function (potential AD; n=5) and 21-hydroxylase Ab positive patients with impaired adrenal function (subclinical AD; n=5) (see Table 3). Pool positive serum prepared from ten 21-hydroxylase Ab positive patients with AD (21-hydroxylase Ab levels ranging from 7 to 22 units/nL) was used in some experiments. Pool serum from twenty healthy blood donors was used as a negative control.

Immunofluorescence Studies

Classical indirect immunofluorescence tests were carried out using thin cryosections of human and bovine adrenal tissue and fluoresceine isotihiocyanate-conjugated anti-mouse IgG.

Analysis of Reactivity of 21-OH MAb with Modified 21-OH Proteins

Modified $^{35}$-S-labelled 21-hydroxylase proteins containing various deletions and truncations (see Tables 1 and 2, and FIG. 1) were produced in the in vitro transcription/translation (TnT; Promega) system and were used in an immunoprecipitation assay (IPA) to assess 21-hydroxylase MAb binding. The TnT reactions were carried out with a methionine-free rabbit reticulocyte lysate in the presence of $^{35}$-S-methionine (10Ci/L; Amersham). The reaction mixture was then passed through a 0.5×16 cm column of Sephadex G50 (Pharmacia), eluted with 150mmol/L Tris buffer pH8.3, containing (per liter) 200mmol of NaCl, 10 mL of Tween 20 and 10 g of bovine serum albumin (thereafter called Tris buffer); 1 mL fractions were collected. The fractions collected were tested for reactivity with 21-OH antibodies by IPA, diluted to give about 30,000 counts/min per 50μL and stored in aliquots at −70° C. Synthesis of proteins coded for by the various constructs was assessed by analysis on polyacrylamide gels (9%) in sodium dodecyl sulphate (SDS) followed by autoradiography.

The IPA was carried out with a 96-well filtration plate system incorporating 0.45μm (pore size) filters (Multiscreen, Milipore UK Limited) as described before. Aliquots of 50μL of $^{35}$-S-21-OH were incubated with aliquots of antibody (50μL) for two hours at room temperature with shaking. To each microtiter well was then added 50μL of anti-mouse IgG-agarose (Sigma), diluted 5 fold in Tris buffer and the samples were incubated for one hour more at room temperature with shaking. The plate was then placed on a suction unit (Millipore UK) and the immune complexes bound to anti-mouse IgG agarose were washed three times with 200μL of Tris buffer. After this washing, the bottom of each well was punched out into vials containing 1 mL of scintillation liquid (Ultima Gold, Packard) and the radioactivity counted in a scintillation counter. A negative control MAb was included in each assay as well as rabbit 21-hydroxylase Ab as a control. Each experiment was carried out in duplicate and binding to each modified 21-hydroxylase protein was carried out in two separate experiments.

Effects of Fab or F(ab')$_2$ Preparations on the Binding of Intact Monoclonal 21-OH IgG and 21-OH Abs to $^{125}$I-21-OH Further analysis of the epitopes recognised by the 21-hydroxylase MAbs and by 21-hydroxylase Abs was carried out using a technique which exploits the ability of protein A to bind to intact antibody complexed with $^{125}$-I labelled antigen, but not to Fab or F(ab')$_2$ bound to labelled antigen.

Fab or F(ab')$_2$ preparations, at various dilutions, were incubated for seven hours at 4° C. with $^{125}$-I-labelled 21-hydroxylase (30,000 cpm/50μL). Intact 21-hydroxylase antibodies (either 50μL 21-OH MAb IgG or 50μL patient sera appropriately diluted in assay buffer) were then added and incubation continued for eighteen hours at 4° C. $^{125}$I-labelled 21-hydroxylase bound to either intact 21-hydroxylase MAb or 21-hydroxylase Ab were separated by the addition of solid phase protein A.

Computer Analysis of Epitope Region Amino Acid Sequences

The complete cDNA sequences of human and bovine 21-hydroxylase were translated into amino acid sequences using the computer software DNASIS v 2.1 (Hitachi Software Engineering America Limited). The amino acid sequences of the epitope regions in both human and bovine 21-hydroxylase were aligned using the Clustal Method.

Statistical Methods

Statistical analyses were carried out using SPSS for Windows software. The statistical significance of any difference of the effect of Fab or F(ab')$_2$ preparations on 21-hydroxylase Ab binding between different forms of autoimmune adrenal disease patient groups was determined by Mann-Whitney U Test.

Results

When tested by immunofluorescence, IgGs from all five MAbs reacted with human adrenal tissue and showed positive staining pattern typical for adrenal cortex antibody. MAb 1 and 2 showed positive staining when bovine adrenal tissue was used, whereas MAb 3,4 and 5 were negative in the immunofluorescence test based on bovine adrenal tissue.

Table 3 shows the characteristics of mouse monoclonal antibodies to 21-hydroxylase.

TABLE 3

| 21-OH McAb | Recombinant Immunogen | Subclass/ Light chain | Affinity constants | Epitope Region (AA) | Species of adrenal tissue used in IFT |
|---|---|---|---|---|---|
| M21-OH1 | 21-OH7 (165-379AA del.) | IgG2a/K | $7.0 \times 10^8$ $M^{-1}$ | ER1 (391–405) | Human (+) Bovine (+) |
| M21-OH2 | 21-OH1-GST (1-494AA) | IgG1/K | $6.1 \times 10^8$ $M^{-1}$ | ER1 (391–405) | Human (+) Bovine (+) |
| M21-OH3 | 21-OH1-GST (1-494AA) | IgG1/K | $2.6 \times 10^8$ $M^{-1}$ | ER2 (406–411) | Human (+) Bovine (−) |
| M21-OH4 | 21-OH1-GST (1-494AA) | IgG1/K | $2.0 \times 10^8$ $M^{-1}$ | ER2 (406–411) | Human (+) Bovine (−) |
| M21-OH5 | 21-OH1-GST (1-494AA) | IgG1/K | $2.3 \times 10^7$ $M^{-1}$ | ER3 (335–339) | Human (+) Bovine (−) |

F(ab')$_2$ fragments were isolated from MAb 1 and 5 whereas Fab fragments were isolated from MAb 3 and the TSHR MAb and these preparations were used in the binding inhibition studies with all five MAbs. These studies showed that the 21-hydroxylase MAbs could be classified into three groups.

Group I:- MAb 1 and 2 which bound to the same epitope region (ER1) on 21-hydroxylase;

Group II:- MAb 3 and 4 which both bound to a different region (ER2); and

Group III:- MAb 5 which recognised a third region (ER3).

Figure 2:
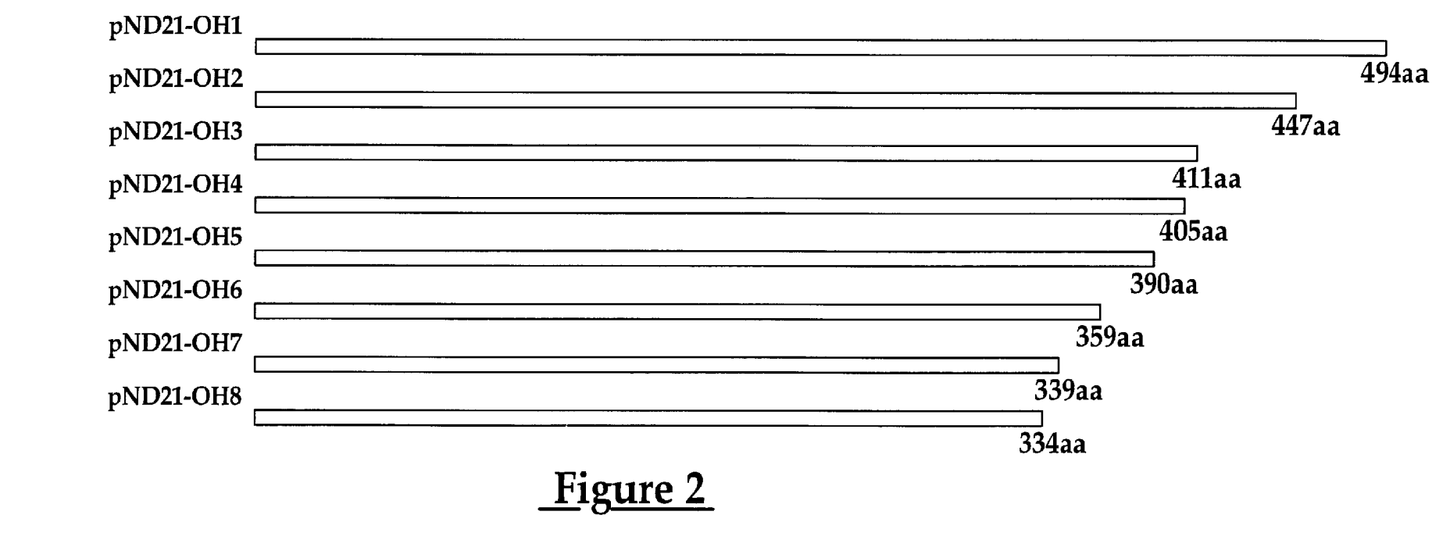
FIG. 2 is a schematic representation of an experimentally produced series of deletions in cDNA encoding 21-hydroxylase.

Inhibition studies using pooled patient sera and Fab or F(ab')$_2$ preparations representative of each MAb group (MAb 1,3 and 5) suggested that 21-hydroxylase Abs recognise epitopes on 21-hydroxylase similar to those recognised by the MAbs (FIG. 2).

Binding of the Ab in pooled patient sera to $^{125}$I-21-hydroxylase was only slightly inhibited (up to 15%) by MAb 1 F(ab')$_2$, but by up to 52% with MAb 3 Pab and up to 74% by MAb 5 F(ab')$_2$ (see FIG. 2). A combination of three Fab or F(ab') (Fab mixture) inhibited 21-hydroxylase binding by Ab in a pooled patient sera by up to 88%. The control Fab inhibited binding of patient Ab to $^{125}$I-21-hydroxylase up to 15% (FIG. 2).

Fab or F(ab')$_2$ preparations from Mab1, 3 and 5 were also used in inhibition studies with individual 21-hydroxylase Ab positive sera. The results of these studies are shown below in Table 4 and are expressed as a percent inhibition of $^{125}$I-21-hydroxylase binding relative to binding of Ab in the absence of Fab or F(ab')$_2$ preparations.

TABLE 4

| | | | | | | % Inhibition of $^{125}$I-21-OH binding | | | |
|---|---|---|---|---|---|---|---|---|---|
| Patient | Sex | Age | Diagnosis | ACA titre | 21-OH Ab (unit/ml) | F(ab')$_2$1 (100 µg/ml) | Fab3 (100 µg/ml) | F(ab')$_2$5 (100 µg/ml) | Fab Mixture (200 µg/ml) |
| 1 | F | 45 | APS I | >320 | 67.5 | 23 | 48 | 77 | 93 |
| 2 | F | 44 | APS I | 320 | 3.3 | 3 | 53 | 85 | 85 |
| 3 | F | 39 | APS I | 80 | 32.3 | 21 | 75 | 84 | 95 |
| 4 | F | 15 | APS I | 80 | 41.2 | 5 | 43 | 82 | 85 |
| 5 | M | 33 | APS I | + | 15.1 | 4 | 68 | 85 | 87 |

TABLE 4-continued

| | | | | | | % Inhibition of $^{125}$I-21-OH binding | | | |
|---|---|---|---|---|---|---|---|---|---|
| Patient | Sex | Age | Diagnosis | ACA titre | 21-OH Ab (unit/ml) | F(ab')$_2$1 (100 μg/ml) | Fab3 (100 μg/ml) | F(ab')$_2$5 (100 μg/ml) | Fab Mixture (200 μg/ml) |
| 6 | F | 53 | APS II | 256 | 10.7 | 50 | 45 | 53 | 87 |
| 7 | F | 42 | APS II | 516 | 71.2 | 14 | 51 | 78 | 81 |
| 8 | F | 39 | APS II | + | 15.3 | 4 | 66 | 82 | 89 |
| 9 | F | 50 | APS II | + | 22.5 | 12 | 72 | 85 | 91 |
| 10 | F | 51 | APS II | + | 32.8 | 16 | 27 | 92 | 92 |
| 11 | M | 27 | AD | 320 | 20 | 0 | 67 | 83 | 92 |
| 12 | M | 31 | AD | 320 | 44.4 | 2 | 46 | 80 | 90 |
| 13 | F | 28 | AD | + | 78.9 | 30 | 27 | 35 | 67 |
| 14 | F | — | AD | + | 22 | 47 | 42 | 52 | 90 |
| 15 | F | — | AD | + | 10.4 | 8 | 36 | 75 | 80 |
| 16 | F | 35 | potential AD | >320 | 23.4 | 15 | 38 | 73 | 93 |
| 17 | F | 29 | potential AD | >320 | 17.4 | 16 | 65 | 82 | 93 |
| 18 | F | 23 | potential AD | 40 | 46.4 | 16 | 67 | 79 | 94 |
| 19 | F | 63 | potential AD | 4 | 15.7 | 22 | 73 | 75 | 92 |
| 20 | M | 25 | potential AD | 80 | 45.7 | 15 | 67 | 85 | 93 |
| 21 | F | 55 | subclinical AD | 320 | 27 | 13 | 41 | 83 | 92 |
| 22 | F | 33 | subclinical AD | 512 | 34.8 | 22 | 47 | 79 | 87 |
| 23 | F | 26 | subclinical AD | 640 | 76.3 | 14 | 63 | 75 | 87 |
| 24 | M | 32 | subclinical AD | 64 | 42.4 | 6 | 66 | 74 | 90 |
| 25 | F | 66 | subclinical AD | 4 | 16.0 | 3 | 47 | 72 | 80 |

ACA titre = adrenal cortex autoantibody (measured by immmunofluorescence)
21-OHAb = 21-OH autoantibodies levels measured by immunoprecipitation assay according to Tanaka et al; J. Clin Endocr. Metab 82 (1997) 1440–1446.

In the majority of patients, the binding of Ab to $^{125}$I-21-OH was not or only partially inhibited by MAb 1 F(ab')$_2$ with a mean inhibition of 15%±12.7 (mean±SD, n=25; range 0–50%). However in the case of sera from 3 patients (1 in the APS type II group and 2 in the AD group) MAb 1 F(ab')$_2$ caused inhibition of Ab binding of 50%, 30% and 47%, respectively (see Table 4). MAb 3 Fab resulted in inhibition of Ab binding to $^{125}$I-21- hydroxylase in all 25 patient sera studied with a mean inhibition of 54%±14.5 (mean±SD, n=25; range 27–75%) (see Table 4).

MAb 5 F(ab')$_2$ also inhibited the Ab binding to $^{125}$I-21-hydroxylase in all 25 patient sera with a mean inhibition of 76%±12.4 (mean±SD, n=25; range 35–92%) (see Table 4).

A combination of the three Fab or F(ab')2 preparations resulted in essentially complete inhibition of Ab binding to $^{125}$I-21-hydroxylase in 24 out of 25 patients with a mean inhibition of 89.5%±4.6 (mean±SD, n=24; range 80–95%). However, in the case of one patient in the AD group the combination of three Fab and F(ab')$_2$ preparations resulted in only 67% inhibition (see Table 4).

There were no statistical differences in the effect of each Fab or F(ab')$_2$ fragments on Ab binding between the different patient groups (p>0.05).

However when a combination of all the three Fab or F(ab')$_2$ preparations were used, there were statistically significant differences between the inhibition of Ab binding of the APS type II group and the potential AD group (p=0.01), the AD group and the potential AD group (p=0.01), and the subclinical AD group and the potential AD group (p=0.01); there were no statistically significant differences between the other groups (p>0.05).

In the IPA based on $^{35}$S-labelled 21-hydroxylase, all five MAbs reacted with full length 21-hydroxylase and with 21-hydroxylase truncated at either amino acid 448 or 418 (from constructs p21-OH1, p21-OH2 and p21-OH3; Table 1). In addition, MAb 5 reacted with 21-hydroxylase truncated at amino acid 381 (from construct p21-OH4) and with 21-hydroxylase with the internal deletion 382-414 amino acids (from construct p21-OH12; Table 1). None of the 21-hydroxylase MAbs bound to 21-OH truncated at either amino acid 335 or amino acid 282 (from constructs p21-OH14 and p21-OH5, respectively; see Table 1).

Further studies were carried out using modified 21-hydroxylase proteins, with smaller stretches of amino acids deleted. All the 21-hydroxylase MAbs reacted with 21-hydroxylase with the amino acids 494–412 deleted (from constructs pND21-OH2 and pND21-OH3; see Table 2). MAb 1, 2 and 5 reacted with 21-hydroxylase with the amino acids 494–406 deleted (from construct pND21-OH4; see Table 2) whereas MAb 3 and 4 did not react with this modified protein (see Table 2). MAb 14 did not react with modified 21-hydroxylase proteins truncated at amino acids 391, 360, 340 and 335 (from constructs pND21-OH5-8, respectively; Table 2). In contrast, MAb 5 bound to 21-hydroxylase proteins truncated at amino acid 391, 360 and 340 but not to 21-hydroxylase truncated at amino acid 335 (Table 2).

Consequently, amino acids 391–405 (SEQ ID No: 1 & 2), defined as ER1, appeared important for binding of MAb 1 and MAb 2. Amino acids 406–411 (SEQ ID No: 3 & 4), defined as ER2, appeared important for binding of MAb 3 and MAb 4 and amino acids 335–339 (SEQ ID No: 5 & 6), defined as ER3, appeared important for binding of MAb 5.

Figure 3:
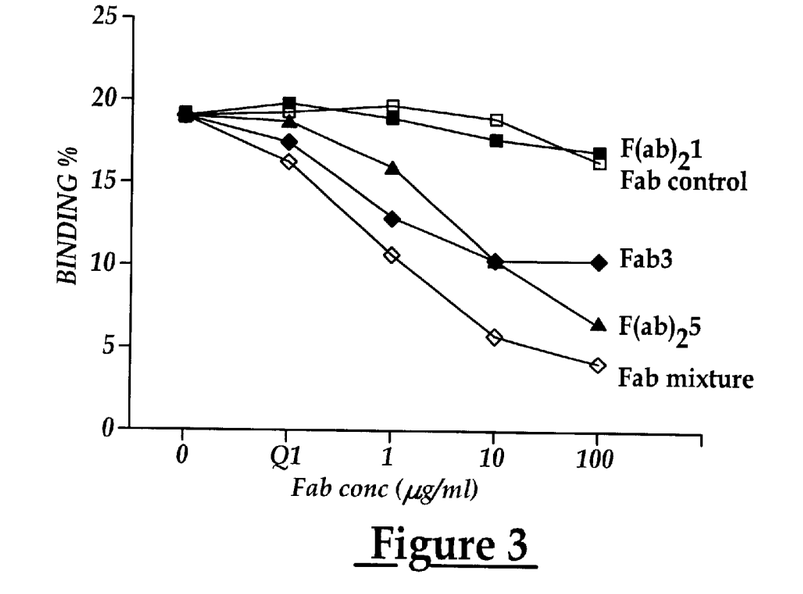
FIG. 3 is a graphical representation of the effect of Fab or F(ab')$_2$ fragments of the monoclonal antibodies described in Table 3; M21-OH1 (F(Ab)$_2$1), M21-OH3(Fab3), M21-OH5 (F(Ab)$_2$5) and a mixture thereof (Fab mixture), on $^{125}I$-labelled 21-hydroxylase binding to intact 21-hydroxylase autoantibodies in a pool of patient sera.
Figure 4:
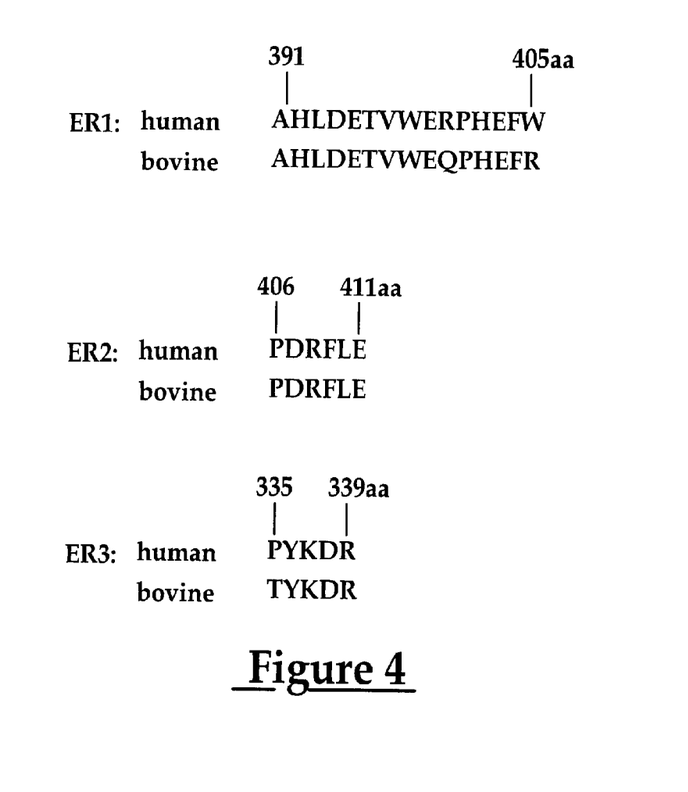
FIG. 4 is a comparison of amino acid sequences (SEQ 10 Nos. 1-6), of the epitope regions in human and bovine 21-hydroxylase.

Computer analysis was carried out on the amino acid sequences of human and bovine 21-hydoxylase, to compare the sequences in the epitope regions ER1, 2 and 3. ER1 (AA 391–405 (SEQ ID No: 1 & 2)) recognized by MAb 1 and MAb 2, was found to be 87% homologous, with 2 amino acid changes; arginine at position 400 in human 21 hydroxylase is changed to glutamine in bovine 21-hydroxylase and tryptophan at position 405 in human 21-hydroxylase is changed to arginine in bovine 21-hydroxylase (FIG. 3). ER2

(AA 406–411 (SEQ ID No: 3 & 4)) recognized by MAb 3 and MAb 4, was found to be 100% homologous. ER3 (AA 335–339 (SEQ ID No: 5 & 6)) recognized by MAb 5, was found to be 80% homologous, with only 1 amino acid different between human and bovine 21-hydroxylase; proline at position 335 in human 21-hydroxylase is changed to threonine in bovine 21-hydroxylase (FIG. 3).

CONCLUSIONS

Consequently, we have identified three stretches of 21-hydroxylase amino acid sequence located in the C-terminal part of the protein which are essential for binding MAbs 1 to 5. As Fab or F(ab')$_2$ fragments prepared from these monoclonal antibodies almost completely inhibited binding of 21-hydroxylase autoantibodies in 24 out of 25 of the sera studied, the same stretches of amino acids must also be essential for autoantibody binding. Autoantibody binding was inhibited to the greatest extent with the MAb 5 F(ab')$_2$, which suggests that ER3 (M 335–339 (SEQ ID No: 5 & 6)) is the most important, autoantigenic epitope in the majority of the patient sera. Studies with Fab or F(ab')$_2$ preparations from MAb 1 and MAb 3 indicated that ER1 (AA 391–405 (SEQ ID No: 1 & 2)) is less important that ER3 (AA 335–339 (SEQ ID No: 5 & 6)) and ER2 (M 406–411 (SEQ ID No: 3 & 4)).

Similar results were obtained when 21-hydroxlase Ab from patients with different forms of autoimmune disease were studied. 21-hydroxylase Ab epitopes dependent on AA 335–339 (ER3) (SEQ ID No: 5 & 6) and AA 406–411 (ER2) (SEQ ID No: 3 & 4) are specific for human 21-hydroxylase and 21-hydroxylase Ab directed to these epitopes do not react with bovine adrenal tissue in immunofluorescence tests. Analyses of differences in the reactivity of MAb with human and bovine adrenal tissue in immunofluorescence studies and the differences in the amino acid sequences of human and bovine 21-hydroxylase suggest that proline 335 is important in forming the major 21-hydroxylase Ab binding site(s).

Overall, these studies show that:

1. The binding of 21-hydroxylase autoantibodies is dependent on at least three different epitopes in the C-terminal part of 21-hydroxylase (AA 335–339 (SEQ ID No: 5 & 6), 391–405 (SEQ ID No: 1 & 2) and 406–411 (SEQ ID No: 3 & 4));
2. Two of these epitopes (one dependent on AA 335–339 (SEQ ID No: 5 & 6) and the other dependent on AA 406–411 (SEQ ID No: 3 & 4) are human 21-hydroxylase specific and a third (AA 391–405 (SEQ ID No: 1 & 2) is present on both human and bovine 21-hydroxylase.

What is claimed is:

1. A method of screening for autoantibodies to 21-hydroxylase in a sample of body fluid obtained from a subject suspected of suffering from, susceptible to, or having autoimmune adrenal disease, said method comprising:

(a) providing said sample of said body fluid from said subject;

(b) contacting said sample with at least one epitope region selected from the group consisting of amino acids 335 to 339 (SEQ ID Nos. 5 or 6) of 21-hydroxylase, amino acids 406 to 411 (SEQ ID Nos. 3 or 4) of 21-hydroxylase and amino acids 391 to 405 (SEQ ID Nos. 1 or 2) of 21-hydroxylase, so as to permit said epitope region to bind to autoantibodies to 21-hydroxylase present in said sample; and (c) monitoring the degree of binding of autoantibodies to 21-hydroxylase present in said sample to said epitope region thereby providing an indication of the presence of autoantibodies to 21-hydroxylase in said sample.

2. A method according to claim 1, wherein step (b) consists of contacting said sample with said epitope region consisting of amino acids 335 to 339 (SEQ ID Nos. 5 or 6) of 21-hydroxylase.

3. A method according to claim 1, wherein step (b) consists of contacting said sample with (i) said epitope region consisting of amino acids 335 to 339 (SEQ ID Nos. 5 or 6) of 21-hydroxylase and (ii) at least one of the further epitope regions 406 to 411 (SEQ ID Nos. 3 or 4) and 391 to 405 (SEQ ID Nos. 1 or 2) of 21-hydroxylase.

4. A method of screening for autoantibodies to 21-hydroxylase in a sample of body fluid obtained from a subject suspected of suffering from, susceptible to, or having autoimmune adrenal disease, said method comprising:

(a) providing said sample of body fluid from said subject;

(b) contacting said sample with an epitope region consisting of amino acids 335 to 339 (SEQ ID Nos. 5 or 6) of 21-hydroxylase so as to permit said epitope region to bind to autoantibodies to 21-hydroxylase present in said sample; and (c) monitoring the degree of binding of autoantibodies to 21-hydroxylase present in said sample to said epitope region thereby providing an indication of the presence of autoantibodies to 21-hydroxylase in said sample.

5. A method according to claim 1, wherein said epitope region is a human derived fragment.

6. A method according to claim 1, wherein said autoimmune adrenal disease comprises Addison's disease or an autoimmune polyglandular syndrome.

7. A method according to claim 1, which further comprises providing one or more monoclonal or polyclonal antibodies directed to said epitope region of 21-hydroxylase as defined in step (b) of claim 1, whereby in step (b) said epitope region of 21-hydroxylase can bind either to said monoclonal or polyclonal antibodies, or to autoantibodies to 21-hydroxylase present in said sample.

8. A method according to claim 4, which further comprises providing one or more monoclonal or polyclonal antibodies directed to said epitope region of 21-hydroxylase as defined in step (b) of claim 4, whereby in step (b) said epitope region of 21-hydroxylase can bind either to said monoclonal or polyclonal antibodies, or to autoantibodies to 21-hydroxylase present in said sample.

9. A method according to claim 7, wherein said monoclonal or polyclonal antibodies are selected from the group consisting of human antibodies, rodent antibodies and recombinant antibodies.

10. A method according to claim 7, which further comprises step (d) wherein:

(d) at least one epitope region of 21-hydroxylase as defined in step (b) of claim 1, and one or more monoclonal or polyclonal antibodies as defined in claim 7, are contacted so as to permit said epitope region to bind to said monoclonal or polyclonal antibodies; and whereby said monitoring in step (c) of claim 1 comprises comparing:

(i) binding of said epitope region and said monoclonal or polyclonal antibodies in step (d) above; with (ii) binding of said epitope region and said monoclonal or polyclonal antibodies in the presence of said sample of body fluid as defined in claim 7;

whereby a decrease in binding in (ii) compared to (i) provides an indication of the presence of autoantibodies to 21-hydroxylase in said sample.

11. A method according to claim 7, which consists of providing at least one monoclonal antibody directed to said epitope region of 21-hydroxylase, whereby, in step (b) of claim 1, said epitope region can bind either to said monoclonal antibody, or to autoantibodies to 21-hydroxylase present in said sample.

12. A method according to claim 7, wherein said epitope region of 21-hydroxylase is substantially immobilized to a solid phase.

13. A method according to claim 7, wherein said monoclonal or polyclonal antibodies are substantially immobilized to a solid phase.

14. A method according to claim 7, wherein the presence of autoantibodies to 21-hydroxylase in said sample provides a diagnosis of said autoimmune disease.

15. A method according to claim 1, wherein binding of said epitope region of 21-hydroxylase and autoantibodies to 21-hydroxylase present in said sample as defined in step (b) of claim 1 is directly monitored in step (c) of claim 1 to provide an indication of the presence of autoantibodies to 21-hydroxylase in said sample.

16. A method according to claim 15, wherein said epitope region of 21-hydroxylase is substantially immobilized to a solid phase.

17. A method according to claim 15, wherein the presence of autoantibodies to 21-hydroxylase in said sample provides a diagnosis of said autoimmune disease.

18. A method of diagnosing overt, subclinical or potential autoimmune adrenal disease in a subject suspected of suffering from, susceptible to, or having said autoimmune adrenal disease, said method comprising:
   (a) providing a sample of body fluid from said subject;
   (b) providing at least one epitope region of 21-hydroxylase selected from the group consisting of amino acids 335 to 339 (SEQ ID Nos: 5 or 6) of 21-hydroxylase, amino acids 406 to 411 (SEQ ID Nos: 3 or 4) of 21-hydroxylase and amino acids 391 to 405 (SEQ ID Nos: 1 or 2) of 21-hydroxylase;
   (c) providing one or more monoclonal or polyclonal antibodies directed to said epitope region of 21-hydroxylase as defined in step (b);
   (d) contacting said sample of body fluid as defined in step (a), said epitope region of 21-hydroxylase as defined in step (b) and said monoclonal or polyclonal antibodies as defined in step (c), so as to permit said epitope region of 21-hydroxylase to bind either to said monoclonal or polyclonal antibodies, or to autoantibodies to 21-hydroxylase present in said sample; and
   (e) monitoring the degree of binding of autoantibodies to 21-hydroxylase present in said sample to said epitope region thereby providing an indication of the presence of autoantibodies to 21-hydroxylase in said sample, the presence of said autoantibodies to 21-hydroxylase in said sample being indicative of said autoimmune adrenal disease.

19. A method according to claim 18, wherein step (b) consists of providing said epitope region consisting of amino acids 335 to 339 (SEQ ID Nos. 5 or 6) of 21-hydroxylase.

20. A method according to claim 18, wherein step (b) consists of providing (i) said epitope region consisting of amino acids 335 to 339 (SEQ ID Nos. 5 or 6) of 21-hydroxylase and (ii) at least one of the further epitope regions 406 to 411 (SEQ ID Nos. 3 or 4) and 391 to 405 (SEQ ID Nos. 1 or 2) of 21-hydroxylase.

21. A method of diagnosing overt, subclinical or potential autoimmune adrenal disease in a subject suspected of suffering from, susceptible to, or having said autoimmune adrenal disease, said method comprising:
   (a) providing a sample of body fluid from said subject;
   (b) providing an epitope region of 21-hydroxylase consisting of amino acids 335 to 339 (SEQ ID Nos. 5 or 6) of 21-hydroxylase;
   (c) providing one or more monoclonal or polyclonal antibodies directed to said epitope region of 21-hydroxylase as defined in step (b);
   (d) contacting said sample of body fluid as defined in step (a), said epitope region of 21-hydroxylase as defined in step (b) and said monoclonal or polyclonal antibodies as defined in step (c), so as to permit said epitope region of 21-hydroxylase to bind either to said monoclonal or polyclonal antibodies, or to autoantibodies to 21-hydroxylase present in said sample; and
   (e) monitoring the degree of binding of autoantibodies to 21-hydroxylase present in said sample to said epitope region thereby providing an indication of the presence of autoantibodies to 21-hydroxylase in said sample, the presence of said autoantibodies to 21-hydroxylase in said sample being indicative of said autoimmune adrenal disease.

22. A method according to claim 18, wherein said epitope region is a human derived fragment.

23. A method according to claim 18, wherein said autoimmune adrenal disease comprises Addison's disease or an autoimmune polyglandular syndrome.

24. A method according to claim 18, wherein said monoclonal or polyclonal antibodies are selected from the group consisting of human antibodies, rodent antibodies and recombinant antibodies.

25. A method according to claim 18, which further comprises step (f) wherein:
   (f) at least one epitope region of 21-hydroxylase as defined in step (b) of claim 18, and one or more monoclonal or polyclonal antibodies as defined in step (c) of claim 18, are contacted so as to permit said epitope region to bind to said monoclonal or polyclonal antibodies; and
whereby said monitoring in step (e) of claim 18 comprises comparing:
   (i) binding of said epitope region and said monoclonal or polyclonal antibodies in step (f) above; with
   (ii) binding of said epitope region and said monoclonal or polyclonal antibodies in the presence of said sample of body fluid as defined in step (d) of claim 18;
whereby a decrease in binding in (ii) compared to (i) provides an indication of the presence of autoantibodies to 21-hydroxylase in said sample.

26. A method according to claim 18, which consists of providing at least one monoclonal antibody directed,t said epitope region of 21-hydroxylase, whereby, in step (d) of claim 18, said epitope region can bind either to said monoclonal antibody, or to autoantibodies to 21-hydroxylase present in said sample.

27. A method according to claim 18, wherein said epitope region of 21-hydroxylase is substantially immobilized to a solid phase.

28. A method according to claim 18, wherein said monoclonal or polyclonal antibodies are substantially immobilized to a solid phase.

29. A method of diagnosing overt, subclinical or potential autoimmune adrenal disease in a subject suspected of suffering from, susceptible to, or having said autoimmune adrenal disease, said method comprising:

(a) providing a sample of body fluid from said subject;

(b) providing at least one epitope region of 21-hydroxylase selected from the group consisting of amino acids 335 to 339 (SEQ ID Nos. 5 or 6) of 21-hydroxylase, amino acids 406 to 411 (SEQ ID Nos. 3 or 4) of 21-hydroxylase and amino acids 391 to 405 (SEQ ID Nos. 1 or 2) of 21-hydroxylase;

(c) contacting said sample of body fluid as defined in step (a) and said epitope region of 21-hydroxylase as defined in step (b), so as to permit said epitope region of 21-hydroxylase to bind to autoantibodies to 21-hydroxylase present in said sample; and (d) directly monitoring the degree of binding in step (c) of autoantibodies to 21-hydroxylase present in said sample to said epitope region thereby providing an indication of the presence of autoantibodies to 21-hydroxylase in said sample, the presence of said autoantibodies to 21-hydroxylase in said sample being indicative of said autoimmune adrenal disease.

30. A method according to claim 29, wherein step (b) consists of providing said epitope region consisting of amino acids 335 to 339 (SEQ ID Nos. 5 or 6) of 21-hydroxylase.

31. A method according to claim 29, wherein step (b) consists of providing (i) said epitope region consisting of amino acids 335 to 339 (SEQ ID Nos. 5 or 6) of 21-hydroxylase and (ii) at least one of the further epitope regions 406 to 411 (SEQ ID Nos. 3 or 4) and 391 to 405 (SEQ ID Nos. 1 or 2) of 21-hydroxylase.

32. A method of diagnosing overt, subclinical or potential autoimmune adrenal disease in a subject suspected of suffering from, susceptible to, or having said autoimmune adrenal disease, said method comprising:

(a) providing a sample of body fluid from said subject;

(b) providing an epitope region of 21-hydroxylase consisting of amino acids 335 to 339 (SEQ ID Nos. 5 or 6) of 21-hydroxylase;

(c) contacting said sample of body fluid as defined in step (a) and said epitope region of 21-hydroxylase as defined in step (b), so as to permit said epitope region of 21-hydroxylase to bind to autoantibodies to 21-hydroxylase present in said sample; and (d) directly monitoring the degree of binding in step (c) of autoantibodies to 21-hydroxylase present in said sample to said epitope region thereby providing an indication of the presence of autoantibodies to 21-hydroxylase in said sample, the presence of said autoantibodies to 21-hydroxylase in said sample being indicative of said autoimmune adrenal disease.

33. A method according to claim 29, wherein said epitope region is a human derived fragment.

34. A method according to claim 29, wherein said autoimmune adrenal disease comprises Addison's disease or an autoimmune polyglandular syndrome.

35. A method according to claim 29, wherein said epitope region of 21-hydroxylase is substantially immobilized to a solid phase.

* * * * *